United States Patent
Berges

(10) Patent No.: US 6,939,340 B1
(45) Date of Patent: Sep. 6, 2005

(54) TAMPON WITH ADJACENT WIDE AND NARROW RAISED PORTIONS

(75) Inventor: Christine Berges, Vernier (CH)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/851,436

(22) Filed: May 21, 2004

(51) Int. Cl.[7] ............................................. A61F 13/20
(52) U.S. Cl. ............ 604/904; 604/385.17; 604/385.18; 604/385.01
(58) Field of Search ........................... 604/904, 385.17, 604/385.18, 385.01; D24/141, 125

(56) References Cited

U.S. PATENT DOCUMENTS

| | | | |
|---|---|---|---|
| 2,123,750 A | | 7/1938 | Schulz |
| 2,553,000 A | * | 5/1951 | Parish ........................ 604/363 |
| 3,738,364 A | | 6/1973 | Brien et al. |
| 3,854,481 A | | 12/1974 | Messing |
| 3,946,737 A | | 3/1976 | Kobler |
| 4,027,673 A | * | 6/1977 | Poncy et al. ................ 604/369 |
| 4,326,527 A | | 4/1982 | Wollangk et al. |
| 4,591,523 A | | 5/1986 | Thompson |
| 4,609,518 A | | 9/1986 | Curro et al. |
| 4,629,643 A | | 12/1986 | Curro et al. |
| 4,685,178 A | | 8/1987 | Nakanishi |
| 4,839,216 A | | 6/1989 | Curro et al. |
| 4,951,368 A | | 8/1990 | Heinen |
| 5,153,971 A | | 10/1992 | Van Iten |
| 5,350,371 A | | 9/1994 | Van Iten |
| 5,387,206 A | * | 2/1995 | Valentine et al. ........... 604/358 |
| 5,592,725 A | | 1/1997 | Brinker |
| 5,788,910 A | | 8/1998 | McNeilis et al. |
| 5,832,576 A | | 11/1998 | Leutwyler et al. |
| 5,891,081 A | | 4/1999 | McNelis et al. |
| 5,911,712 A | | 6/1999 | Leutwyler et al. |
| 5,958,321 A | | 9/1999 | Schoelling et al. |
| 6,003,216 A | | 12/1999 | Hull, Jr. et al. |
| 6,071,259 A | | 6/2000 | Steiger et al. |
| 6,156,021 A | | 12/2000 | Tojkander |
| 6,283,952 B1 | * | 9/2001 | Child et al. ................. 604/540 |
| 6,310,269 B1 | | 10/2001 | Friese et al. |
| 6,433,246 B1 | * | 8/2002 | Nguyen et al. ............. 604/375 |
| 6,758,839 B2 | * | 7/2004 | Lochte et al. .......... 604/385.18 |
| 2002/0151859 A1 | | 10/2002 | Schoelling |
| 2002/0157222 A1 | * | 10/2002 | Friese et al. .................. 28/118 |
| 2003/0167048 A1 | * | 9/2003 | Policappelli ........... 604/385.17 |

FOREIGN PATENT DOCUMENTS

| | | | | |
|---|---|---|---|---|
| EP | 0 422 660 B1 | 2/1994 | | |
| WO | WO 00/37013 A1 | 6/2000 | | |
| WO | WO0143679 A1 | * | 6/2001 | ........... A61F 13/20 |
| WO | WO 01/66055 A1 | 9/2001 | | |
| WO | WO 02/078586 A2 | 10/2002 | | |

* cited by examiner

*Primary Examiner*—Larry I. Schwartz
*Assistant Examiner*—Keshia Gibson
(74) *Attorney, Agent, or Firm*—Bridget D. Murray; Ingrid N. Hickman

(57) ABSTRACT

A tampon for feminine hygiene having an insertion end, a withdrawal end, a longitudinal axis, and an outer surface. The tampon has a compressed fibrous material. The outer surface of the tampon has a first raised portion adjacent to a second raised portion. The first raised portion has a first width dimension and the second raised portion has a second width dimension The first width dimension is greater than said second width dimension.

11 Claims, 2 Drawing Sheets tampon
TAMPON WITH ADJACENT WIDE AND NARROW RAISED PORTIONS

FIELD OF THE INVENTION

This invention relates to a tampon comprising a plurality of raised portions.

BACKGROUND OF THE INVENTION

A wide variety of absorbent catamenial tampons have long been known in the art. It is known that the surface characteristics of a tampon may be altered physically and/or chemically to confer both aesthetic and functional benefits. The surface of tampons can be altered to have non-uniform surface topography. Some examples of tampons with non-uniform topography include a tampon that has absorbent filaments such as in U.S. Pat. No. 3,695,270 issued to Dostal on Oct. 3, 1972, and a tampon with a braided or rope shaped body such as in U.S. Pat. No. 4,361,151 issued to Fitzgerald on Nov. 20, 1982 and U.S. Pat. No. 4,328,804 issued to Shimatani on May 11, 1982. Other tampons comprise longitudinal ribs on the outer surface such as in U.S. Pat. No. 5,403,300 issued to Howarth on Apr. 4, 1995, U.S. Pat. No. 5,592,725 issued to Brinker on Jan. 14, 1997, and U.S. Pat. No. 5,718,675 issued to Leijd on Feb. 17, 1998 and a tampon having spiral grooves on the outer surface such as in WO 02/078586 published on Oct. 10, 2002. While it has been found that these tampons perform their intended function tolerably well, even the best of them do not always imbibe menstrual fluid at a rate sufficient to provide good coverage against leakage. The present invention has been designed to achieve these goals while also providing an aesthetically pleasing exterior appearance for the wearer.

SUMMARY OF THE INVENTION

The present invention relates to a tampon for feminine hygiene comprising an insertion end, a withdrawal end, a longitudinal axis, and an outer surface. The tampon is comprised of compressed fibrous material. The outer surface of the tampon comprises a first raised portion adjacent to a second raised portion. The first raised portion has a first width dimension and the second raised portion has a second width dimension The first width dimension is greater than the second width dimension.

DETAILED DESCRIPTION OF THE INVENTION

Figure 1:
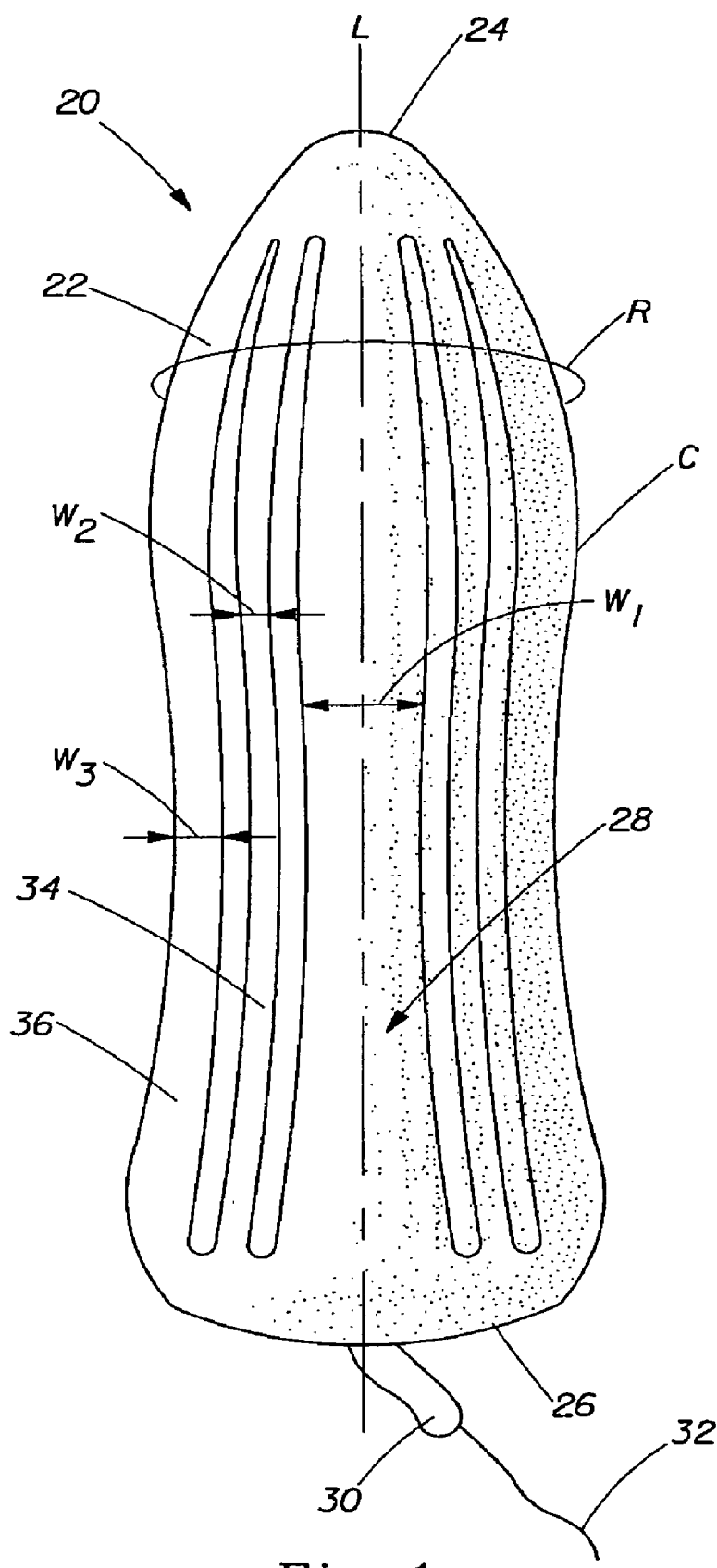
FIG. 1 is a plan view of the tampon of the present invention having a plurality of raised portions.

As used herein "applicator" refers to a device or implement that facilitates the insertion of a tampon, medicament, treatment device, visualization aid, or other into an external orifice of a mammal, such as the vagina, rectum, ear canal, nasal canal, or throat. Non-limiting specific examples of such include any known hygienically designed applicator that is capable of receiving a tampon may be used for insertion of a tampon, including the so-called telescoping, tube and plunger, and the compact applicators, an applicator for providing medicament to an area for prophylaxis or treatment of disease, and the like.

As used herein, the term "bicomponent fibers" refers to fibers that have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement, a pie arrangement or an "islands-in-the-sea" arrangement.

The term "center region" refers to the portion of the tampon located 5 mm on either side on the geometrical center of the longitudinal axis between the insertion end and the withdrawal end.

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

The term "cross-section" as used herein, is any 5 mm thick section of the tampon orthogonal to the longitudinal axis.

As used herein, the term "density" is used with its common technical meaning with units of $g/cm^3$ or g/cc. The density may refer specifically to that of a specific region or feature of the tampon as noted. The density will be measured, unless otherwise noted, by taking the weight divided by the geometric volume described by the shape. Unless noted, density refers to that of the overall structure and not the individual components, and will include in the measurement void volume of small pores and voids within the overall structure.

The term "digital tampon" refers to a tampon which is intended to be inserted into the vaginal canal with the user's finger and without the aid of an applicator. Thus, digital tampons are typically visible to the consumer prior to use rather than being housed in an applicator.

The term "folded" as used herein, is the configuration of the tampon pledget that may be incidental to lateral compaction of the absorbent material or may purposely occur prior to a compression step. Such a configuration is readily recognizable, for example, when the absorbent material abruptly changes direction such that one part of the absorbent material bends and lies over another part of the absorbent material.

As used herein, "generally cylindrical" refers to the usual shape of tampons as is well known in the art, but which also includes oblate or partially flattened cylinders, curved cylinders, and shapes which have varying cross-sectional areas (such as a Coke™ bottle shape). The longitudinal axis refers to the longest linear dimension of the tampon. The cross-section refers to a slice taken at right angles to the longitudinal axis.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

As used herein, the term "longitudinal axis" of a tampon refers to the axis that runs through the center of the tampon as shown in FIG. 1. A portion of the tampon may be asymmetric about the longitudinal axis, such as when the withdrawal end region is flared and distorted from the original shape of the rest of the tampon (such as a "fin shape"). Further, the longitudinal axis may be linear or non-linear.

The "outer surface" of a tampon refers to the visible surface of the (compressed and/or shaped) tampon prior to use and/or expansion. At least part of the outer surface may be smooth or alternatively may have topographic features, such as ribs, spiraling ribs, a mesh pattern, or other topographical features. Typically, tampons are constructed from an absorbent material, which has been compressed and/or shaped in any or all of the width direction, the radial direction, and the axial direction, in order to provide a tampon which is of a size and stability to allow insertion within the vagina or other body cavity.

As used herein, the terms "pledget" or "tampon pledget" are intended to be interchangeable and refer to a construction of absorbent material prior to the compression and/or shaping of such construction into a tampon as described above. Pledgets may be rolled, folded or otherwise manipulated prior to compression. Tampon pledgets are sometimes referred to as tampon blanks, or a softwinds, and the term "pledget" is intended to include such terms as well. In general in this specification, the term "tampon" is used to refer to a finished tampon after the compression and/or shaping process. It will be recognized by those of skill in the art that in some contexts these terms are interchangeable. The different stages of tampon manufacture are described herein with an eye toward providing the greatest possible clarity. Therefore, the terms used are to assist the reader in best understanding the features of the invention and not to introduce limitations in the terms not consistent with the context in which they are used in this specification.

As used herein, the term "radial axis" of a tampon refers to the axis that runs at right angles to the longitudinal axis of the tampon as shown in FIG. 1.

The term "rolled," as used herein, is the configuration of the tampon pledget after winding the absorbent material upon itself.

As used herein, a tampon has a "self-sustaining shape" when a tampon pledget has been compressed and/or shaped such that it assumes a general shape and size, which is vaginally insertable, absent external forces. It will be understood by one of skill in the art that this self-sustaining shape need not, and preferably does not persist during actual use of the tampon. That is, once the tampon is inserted and begins to acquire fluid, the tampon may begin to expand and may lose its self-sustaining form.

As used herein, the term "tampon," refers to any type of absorbent structure that is inserted into the vaginal canal or other body cavities for the absorption of fluid therefrom, to aid in wound healing, or for the delivery of active materials, such as medicaments, or moisture. The tampon may be compressed into a generally cylindrical configuration in the radial direction, axially along the longitudinal axis or in both the radial and axial directions. While the tampon may be compressed into a substantially cylindrical configuration, other shapes are possible. These may include shapes having a cross section that may be described as rectangular, triangular, trapezoidal, semi-circular, hourglass, serpentine, or other suitable shapes. Tampons have an insertion end, withdrawal end, a length, a width, a longitudinal axis, a radial axis and an outer surface. The tampon's length can be measured from the insertion end to the withdrawal end along the longitudinal axis. A typical compressed tampon for human use is 30–60 mm in length. A tampon may be straight or non-linear in shape, such as curved along the longitudinal axis. A typical compressed tampon is 8–20 mm wide. The width of a tampon, unless otherwise stated in the specification, corresponds to the length across the largest cylindrical cross-section, along the length of the tampon.

The term "vaginal cavity," "within the vagina," and "vaginal interior," as used herein, are intended to be synonymous and refer to the internal genitalia of the mammalian female in the pudendal region of the body. The term "vaginal cavity" as used herein is intended to refer to the space located between the introitus of the vagina (sometimes referred to as the sphincter of the vagina or hymeneal ring,) and the cervix. The terms "vaginal cavity," "within the vagina" and "vaginal interior," do not include the interlabial space, the floor of vestibule or the externally visible genitalia.

FIG. 1 shows a tampon 20 of the present invention. The tampon 20 can be any shape in the art and any type of tampon known in the art. FIG. 1 shows a shaped tampon, such as that disclosed in currently pending and commonly assigned, U.S. patent application Ser. No. 10/150,050, filed Mar. 18, 2002, entitled "Substantially Serpentine Shaped Tampon," to Randall, et al., and currently pending and commonly assigned, U.S. patent application Ser. No. 10/150,055, filed Mar. 18, 2002, entitled "Shaped Tampon," to Kollowitz, et al. FIG. 1 illustrates a tampon for feminine hygiene, having an outer surface 22, an insertion end 24, a withdrawal end 26, a center region C, a radial axis R, and a longitudinal axis L. The fibrous material of the tampon 20 of the present invention may have uniform density over a cross section of the tampon 20. Alternatively, fibrous material of the tampon 20 of the present invention may have varying density over a cross section of the tampon 20. A tampon 20 having varying densities is described in greater detail in co-pending patent application Ser. No. 10/700,776 filed Nov. 4, 2003, entitled "Substantially Serpentine Shaped Tampon with Varying Density Regions", to Almond, and co-pending patent application Ser. No. 10/700,775 filed Nov. 4, 2003, entitled "Substantially Serpentine Shaped Tampon with Varying Density Regions", to Almond.

Figure 2:
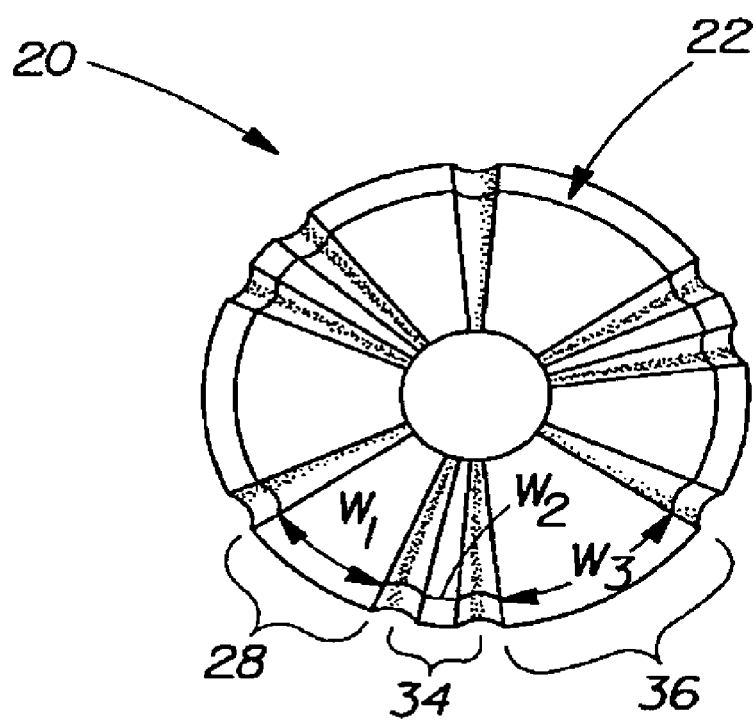
FIG. 2 is a plan view of the insertion end of the tampon of the present invention.

The outer surface 22 of the tampon 20 comprises a first raised portion 29 and a second raised portion 34 such as in FIG. 1 and FIG. 2. The first raised portion 29 and second raised portion 34 on the outer surface 22 of the tampon 20 may project generally outwardly from the outer surface 22, as shown in FIG. 1 and FIG. 2. The first raised portion 29 is adjacent to the second raised portion 34. The first raised portion 29 has a first width dimension $W_1$ The second raised portion 34 has a second width dimension $W_2$. The first width dimension $W_1$ is greater than said second width dimension $W_2$. The tampon 20 may further comprise a third raised portion 36 that comprises a third width dimension $W_3$. The first width dimension $W_1$ is may be equal to the third width dimension $W_3$. The third width dimension $W_3$ may be equal to the first width dimension $W_1$.

The first width dimension $W_1$, second width dimension $W_2$, and third width dimension $W_3$ are measured at the largest width along the longitudinal axis L. The first width dimension $W_1$, second width dimension $W_2$ and third width dimension $W_3$ may vary as measured along the longitudinal axis L, so as long as the width dimension remain proportional. That is, first width dimension $W_1$ remains greater than the second width dimension $W_2$ and the third width dimension $W_3$ may be equal to the first width dimension $W_1$. The first width dimension $W_1$, second width dimension $W_2$ and third width dimension $W_3$ may vary continuously or intermittently as measured along the along the longitudinal axis L. The first width dimension $W_1$, second width dimension $W_2$, and third width dimension $W_3$ may have the largest widths at the insertion end 24. The first width dimension $W_1$, second width dimension $W_2$, and third width dimension $W_3$ may have the largest widths at the withdrawal end 26. The first width dimension $W_1$, second width dimension $W_2$ and third width dimension $W_3$ may have the smallest widths at the center region C. The first width dimension $W_1$, as measured adjacent to the outer surface 22, may have a range from about 2.5 mm to about 15.5 mm. The second width dimension $W_2$ and third width dimension $W_3$, as measured adjacent to the outer surface 22, may range from about 0.5 mm to about 2 mm. The first raised portion 29 second raised portion 34, and third raised portion 36 also have an amplitude as measured orthogonal to the outer surface 22 of from about 0.1 mm to about 3 mm FIG. 2 is plane view of insertion end 24 of tampon 20 that illustrates the first raised portion 29 is adjacent to the second raised portion 34 and the third raised portion 36 is adjacent to the second raised portion 34. The first raised portion 29 has a first width dimension $W_1$ The second raised portion 34 has a second width dimension $W_2$. The third raised portion 36 has a third width dimension $W_3$. The first width dimension $W_1$ is greater than the second width dimension $W_2$. The third width dimension $W_3$ is equal to the first width dimension $W_1$.

Not to be bound by theory, it is believed that the topographic feature of the present tampon 20 increases the surface area of the tampon 20 allowing for improved fluid imbibition, thus, providing improved coverage against leakage.

The plurality of raised portions 28 may be any shape known include amorphous, geometric, or a combination thereof. The raised portions 28 may be symmetric or asymmetric. The raised portions 28 may be any be any two or three-dimensional geometric shape known including but not limited to ovals, circles, rectangles, trapezoids, triangles, cones, squares, spirally shaped, rectangles, quadrilaterals, pentagons, hexagons, heptagons, octagons, nonagons, decagons, parallelograms, rombuses, trapeziums, alphanumerics, animal shapes, trademarks, logos, foreign lanuguages, kanji, ASCII, and mixtures thereof. The raised portions 28 on the outer surface 22 of the tampon 20 may be arranged randomly or in a pattern. The pattern of raised portions 28 on the outer surface 22 of the tampon 20 may be diagonal lines, straight lines, checkerboard and mixtures thereof.

Tampon pledget may be constructed from a wide variety of liquid-absorbing materials commonly used in absorbent articles. Such materials include but are not limited to rayon (such as GALAXY Rayon SARILLE L rayon both available from Acordis Fibers Ltd., of Hollywall, England), cotton, bicomponent fibers, polyethylene, polypropylene, other suitable natural or synthetic fibers known in the art, and mixtures thereof. Other materials that may be incorporated into the tampon pledget including comminuted wood pulp which is generally referred to as airfelt, folded tissues, woven materials, nonwoven webs, peat moss, absorbent foams (such as those disclosed in U.S. Pat. No. 3,994,298 issued to DesMarais on Nov. 30, 1976 and U.S. Pat. No. 5,795,921 issued to Dyer, et al.,) capillary channel fibers (such as those disclosed in U.S. Pat. No. 5,356,405 issued to Thompson, et. al on Oct. 18, 1994), high capacity fibers (such as those disclosed in U.S. Pat. No. 4,044,766 issued Kaczmarzk, et al. on Aug. 30, 1977), superabsorbent polymers or absorbent gelling materials (such as those disclosed in U.S. Pat. No. 5,830,543 issued to Miyake, et al. on Nov. 3, 1998).

The tampon pledget is generally square or rectangular, but other shapes such as trapezoidal, triangular, hemispherical, chevron and hourglass shaped are also acceptable. A more detailed description of liquid-absorbing materials and pledget shapes and dimensions can be found in currently pending and commonly assigned, U.S. patent Ser. No. 10/039,979, filed Oct. 24, 2001, entitled "Improved Protection and Comfort Tampon," to Agyapong, et al. A typical size for tampon pledget prior to compression may be from about 40 mm to about 100 mm in length and from about 40 mm to about 80 mm in width. In general, the pledget material may be from about 40 mm to about 60 mm in length and from about 50 mm to about 70 mm in width. The typical range for the overall basis weight is from about 150 $g/m^2$ to about 800 $g/m^2$. The tampon pledget material may be a laminar structure comprised of integral or discrete layers. Alternatively, the tampon pledget may not have a layered structure at all. The tampon pledget may have or uniform density or in the alternative may have portions that are more or less dense than other portions, such as a core, which is highly compressed.

The tampon 20 of the present invention may optionally comprise an overwrap comprising material such as rayon, cotton, bicomponent fibers, polyethylene, polypropylene, other suitable natural or synthetic fibers known in the art, and mixtures thereof. The tampon 20 may have a nonwoven overwrap comprised of bicomponent fibers that have a polypropylene core surrounded by polyethylene manufactured by Vliesstoffwerke Christian Heinrich Sandler GmbH & Co.KG (Schwarzenbach/Saale, Germany) under the tradename SAS B31812000. The tampon 20 may comprise a nonwoven overwrap of a hydroentangled blend of 50% rayon, 50% polyester available as BBA 140027 produced by BBA Corporation of South Carolina, U.S. The overwrap may be 100% polyester. The overwrap may be treated to be hydrophilic, hydrophobic, wicking or non-wicking. The tampon pledget may also contain a variety of other adjuvants such as odor control agents, antibacterial agents, colorants, indicators for various kinds of illnesses such as yeast infections, indicator features for signaling when the tampon should be changed, and the like.

The tampon of the present invention may comprise a secondary absorbent member. The secondary absorbent member may be comprised of material such as rayon, cotton, bicomponent fibers, polyethylene, polypropylene, polyester, other suitable natural or synthetic fibers known in the art, and mixtures thereof. The secondary absorbent member may be single ply or multiple plies. The secondary absorbent member may be absorbent and/or hydrophilic. The secondary absorbent member 30 may be attached to the second end 38 of the tampon pledget, such that after folding and compression, the secondary absorbent member 30 is attached to the withdrawal end 26 end of the tampon 20. The secondary absorbent member 30 may be arranged in a wide variety of shapes and configurations and may be generally cylindrical, spherical, semi-spherical, disc-like, planar, rectangular, "sheet-like," "skirt-like" in shape. The secondary absorbent member 30 may range in length from about 10 mm to about 40 mm from the withdrawal end 26 of the tampon 20. The secondary absorbent member 30 may be from about 20 mm to about 25 mm in length, from about 6 mm to about 40 mm in width, and from about 0.5 mm to about 5 mm in thickness.

Withdrawal members 32 useful in the present invention may be made of any suitable material known in the prior art and include cotton and rayon. In addition, the withdrawal member 32 can take on other forms such as a ribbon, loop, tab, or the like. The withdrawal member 32 may be integral with the tampon pledget. The withdrawal member 32 or regions of the withdrawal member 32 may be treated to be non-absorbent, absorbent or hydrophilic. The withdrawal member 32 may be attached in any suitable manner known in the art including sewing, adhesive attachment, bonding, thermal bonding, or a combination thereof including the method disclosed in currently pending, commonly assigned, U.S. patent application Ser. No. 10/610,075, filed Jun. 30, 2003, entitled "Method and Apparatus for Cord Attachment" to Sargent, et al.

The tampon 20 of the present invention may be inserted digitally. It may be desirable to provide a finger indent at the withdrawal end 26 of the tampon 20 to aid in insertion, if the tampons 20 are to be digital tampons. An example of a finger indent can be found in U.S. Pat. No. 6,283,952, filed May 5, 1997, entitled "Shaped Tampon," issued to Child, et al.

Alternatively, the insertion may be aided through the use of any applicator adapted from the prior art. Prior art applicators having a typical "tube and plunger" type arrangement may be plastic, paper, or other suitable material. Additionally, a "compact" type applicator is also suitable. Where the tampon 20 of the present invention is shaped and provides aesthetic appeal to consumers, it is may be desirable to combine the shaped tampon with an applicator type which enables the user to observe at least a portion or the whole shape or design of the tampon 20. Two techniques which allow the user to better notice the shape or design of the tampon 20 are to either make visual observation possible through the use of a translucent or even transparent applicator materials, or to provide a tampon applicator insertion end that better follows and hence better displays the profiled shape of the enclosed shaped tampon than the typical commercial tampon applicators comprising straight-walled cylindrical inserter tubes often made from molded plastic or laminated cardboard tubes. These techniques may be found in currently pending and commonly assigned, U.S. patent application Ser. No. 10/150,055, filed Mar. 18, 2002, entitled "Shaped Tampon," to Kollowitz, et al.

The tampons 20 of the present invention can optionally be packaged in wrappers which are loose, conforming, tightly conforming and mixtures thereof to the outer surface 22 of the tampon 20 in order to visually show the consumer the tampon packaged therein. Tightly conforming wrappers are particularly useful when the shaped tampons are intended to be used digitally and therefore are not housed in an applicator prior to use. The wrappers should substantially enclose each individual tampon 20 and are removed prior to insertion and use. "Tightly conforming," means that there is substantially no visually noticeable void space between the wrapper and the tampon 20. In some embodiments of the present invention, some regions of the wrapper material may provide additional functional benefits, such as cord deployment means. Since tampons 20 are typically made by compressing fibrous absorbent material into a self-sustaining shape, the tightly conforming wrapper can optionally be used to act with a certain compressing force on the outer surface 22 of the tampon 20, which will aid in maintaining the self-sustaining shape by counteracting the expansion of the compressed material. Such wrappers are discussed in detail currently pending and commonly assigned, U.S. patent application Ser. No. 10/150,055, filed Mar. 18, 2002, entitled "Shaped Tampon," to Kollowitz.

While several methods of making the tampon 20 of the present invention should be apparent to one of skill in the art in light of the disclosure herein, following is a description of one method of making a tampon 20 of the present invention.

The tampon 20 of the present invention is made by providing the material that comprises the tampon pledget, withdrawal member 32, attaching or joining these components, folding the components and compressing. In making the tampon 20 of the present invention, the tampon pledget is provided. Next, the withdrawal member 32 is provided. The withdrawal member 32 may be attached in any suitable manner known in the art including sewing, adhesive attachment, bonding, thermal bonding, or a combination thereof, including the method disclosed in currently pending, commonly assigned, U.S. patent application Ser. No. 10/610, 075, filed Jun. 30, 2003, entitled "Method and Apparatus for Cord Attachment" to Sargent, et al.

Next, the combination of the tampon pledget, secondary absorbent member 30 and withdrawal member 32 are folded or rolled. To form a tampon ready for use, the tampon pledget is typically compressed and heat conditioned in any suitable conventional manner including the method disclosed in currently pending, commonly assigned, U.S. Patent Application Serial No., filed May 12, 2003, entitled "A Process for Producing Stabilized Tampons," to Prosise, et al. Pressures and temperatures suitable for this purpose are well known in the art. Typically, the tampon pledget may be compressed in both the radial and axial direction using any means well known in the art. While a variety of techniques are known and acceptable for these purposes, a modified tampon compressor machine available from Hauni Machines, Richmond, Va., is suitable. Optionally, a finger indent can be made using a compression rod. An example of a finger indent can be found in U.S. Pat. No. 6,283,952, filed May 5, 1997, entitled "Shaped Tampon" issued to Child, et al. The secondary absorbent member 30 may be attached to the tampon 20 before or after compression, and then no modification of the method of making a conventional compressed absorbent tampon is necessary.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. A tampon for feminine hygiene comprising an insertion end, a withdrawal end, a center region, a longitudinal axis, and an outer surface;

said tampon being comprised of compressed fibrous material;

said outer surface of said tampon comprises a first raised portion and a second raised portion adjacent to said first portion;

said first raised portion comprising a first width dimension;

said second raised portion comprising a second width dimension;

wherein said first raised portion is adjacent to a first non-raised portion, said first non-raised portion is adjacent to said second raised portion;

wherein said first width dimension is greater than said second width dimension along a radial axis;

and wherein first raised portion is not in contact with said second raised portion.

2. The tampon of claim 1 wherein said first width dimension ranges from about 2.5 mm to about 15.5 mm.

3. The tampon of claim 1 wherein said second width dimension ranges from about 0.5 mm to about 2 mm.

4. The tampon of claim 1 wherein said raised portions have an amplitude that ranges from about 0.1 mm to about 3 mm.

5. The tampon according claim 1 further comprising a third raised portion comprising a third width dimension.

6. The tampon according to claim 5 wherein said third width dimension is equal to said third width dimension.

7. The tampon according to claim 1 wherein the fibrous material of said tampon has an essentially uniform density over a cross-section of the tampon.

8. The tampon according to claim 1 wherein the fibrous material of said tampon has varying density over a cross-section of the tampon.

9. The tampon according to claim 1 wherein said tampon further comprises a core which is highly compressed.

10. The tampon according to claim 1 wherein said withdrawal end further comprises a withdrawal member.

11. The tampon according to claim 1 wherein said withdrawal end further comprises a finger indent.

* * * * *